(12) United States Patent
Kajanto

(10) Patent No.: US 10,322,196 B2
(45) Date of Patent: Jun. 18, 2019

(54) HEAT TREATMENT OF A NANOFIBRILLAR CELLULOSE HYDROGEL

(71) Applicant: UPM-KYMMENE CORPORATION, Helsinki (FI)

(72) Inventor: Isko Kajanto, Espoo (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 43 days.

(21) Appl. No.: 15/538,441

(22) PCT Filed: Dec. 21, 2015

(86) PCT No.: PCT/FI2015/050917
§ 371 (c)(1),
(2) Date: Jun. 21, 2017

(87) PCT Pub. No.: WO2016/102765
PCT Pub. Date: Jun. 30, 2016

(65) Prior Publication Data
US 2017/0368211 A1 Dec. 28, 2017

(30) Foreign Application Priority Data
Dec. 22, 2014 (FI) ........................... 20146137

(51) Int. Cl.
*A61L 2/04* (2006.01)
*A61L 27/20* (2006.01)
*B01J 13/00* (2006.01)

(52) U.S. Cl.
CPC ................ *A61L 2/04* (2013.01); *A61L 27/20* (2013.01); *B01J 13/0069* (2013.01); *A61L 2400/12* (2013.01)

(58) Field of Classification Search
CPC .......... A61L 2/04; A61L 27/40; B01J 13/0069
See application file for complete search history.

(56) References Cited

U.S. PATENT DOCUMENTS

| 2001/0004869 A1 | 6/2001 | Cantiani et al. |
| 2003/0032622 A1 | 2/2003 | Ljungquist |

(Continued)

FOREIGN PATENT DOCUMENTS

| EP | 1027835 A1 | 8/2000 |
| JP | 2006333740 A | 12/2006 |

(Continued)

OTHER PUBLICATIONS

Search Report from Patent Application No. 20146137 dated Apr. 21, 2015.

(Continued)

*Primary Examiner* — Sean E Conley
(74) *Attorney, Agent, or Firm* — Nixon Peabody LLP

(57) ABSTRACT

The invention relates to a method for treating a nanofibrillar cellulose hydrogel, wherein the method comprises the steps of: providing a nanofibrillar cellulose hydrogel; and subjecting the nanofibrillar cellulose hydrogel to a heat treatment, wherein the heat treatment is carried out by transferring the nanofibrillar cellulose hydrogel through at least one heat exchanger or through at least one insulated holding tube, during which heat treatment the nanofibrillar cellulose hydrogel is kept at a predetermined temperature within the range of 110-150° C. for a period of time in the range of 15 seconds to 20 minutes, wherein the pre-determined temperature and period of time are chosen such that the number of viable micro-organisms in the nanofibrillar cellulose hydrogel is reduced by a factor of at least $10^3$.

15 Claims, 1 Drawing Sheet

(56) References Cited

U.S. PATENT DOCUMENTS

2014/0322327 A1  10/2014  Laukkanen et al.
2014/0349377 A1  11/2014  Lauraeus et al.

FOREIGN PATENT DOCUMENTS

| | | |
|---|---|---|
| JP | 2010018704 A | 1/2010 |
| WO | 2013072563 A1 | 5/2013 |
| WO | 2013093199 A1 | 6/2013 |
| WO | 2014128354 A1 | 8/2014 |

OTHER PUBLICATIONS

International Search Report from International Application No. PCT/FI2015/050917 dated Mar. 11, 2016.
International Preliminary Report on Patentability from International Application No. PCT/FI2015/050917 dated Mar. 6, 2017.

HEAT TREATMENT OF A NANOFIBRILLAR CELLULOSE HYDROGEL

CROSS-REFERENCE TO RELATED APPLICATIONS

This application is a U.S. National Stage of International Application No. PCT/FI2015/050917, filed on Dec. 21, 2015, which claims priority to Finnish Patent No. 20146137, filed Dec. 22, 2014, the contents of each of which are incorporated herein by reference in their entireties.

FIELD OF THE INVENTION

The invention relates to a method for treating nanofibrillar cellulose hydrogel. The invention further relates a nanofibrillar cellulose hydrogel, to a system for treating a nanofibrillar cellulose hydrogel, and to the use of the nanofibrillar cellulose hydrogel.

BACKGROUND OF THE INVENTION

A nanofibrillar cellulose hydrogel has been found use in different applications such as in cosmetics and pharmaceuticals as well as in cell culture. However, the use thereof in cosmetic or pharmaceutical products or devices put challenges on ensuring that the hydrogel is aseptic or sterile as well as on its other properties that may be affected by the used sterilization procedure.

Generally, sterilization efficiency is defined as the ability to remove or destroy all forms of microbial life, including viruses, bacteria and fungi, under vegetative forms or spores. However, since absolute sterility cannot be verified, the statistical definition of sterility is used in practice, by using the security assurance level (SAL), defined as "the probability of a single viable micro-organism occurring in or on a product after sterilization". The worldwide accepted definition of sterility of medical devices is defined as the chance of finding a viable organism in or on a medical device to be at most 1 in 1000000 or an SAL of at most $10^{-6}$.

The number of viable micro-organisms in nanofibrillar cellulose hydrogel can be reduced or eliminated by subjecting the hydrogel to autoclaving for 20 minutes at a temperature of 121° C. Autoclaving, however, has some challenges as it affects the properties, such as viscosity, of the hydrogel.

The inventors have therefore recognized the need for a method to treat nanofibrillar cellulose hydrogel such that it is suitable for further applications.

PURPOSE OF THE INVENTION

The purpose of the invention is to provide a new type of method for treating nanofibrillar cellulose hydrogel. Further the purpose of the invention is to provide a new type of nanofibrillar cellulose hydrogel and new uses of nanofibrillar cellulose hydrogel. Further the purpose of the invention is to provide a new system for treating nanofibrillar cellulose hydrogel.

SUMMARY

The method according to the present invention is characterized by what is presented in claim 1.

The nanofibrillar cellulose hydrogel according to the present invention is characterized by what is presented in claim 11 or 17.

The system according to the present invention is characterized by what is presented in claim 12.

The use of a heat treatment according to the present invention is characterized by what is presented in claim 16.

The uses of the nanofibrillar cellulose hydrogel are characterized by what is presented in claim 18 or 19.

BRIEF DESCRIPTION OF THE DRAWINGS

The accompanying drawing, which is included to provide a further understanding of the invention and constitutes a part of this specification, illustrate one embodiment of the invention and together with the description helps to explain the principles of the invention. In the drawing.

DETAILED DESCRIPTION OF THE INVENTION

Figure 1:
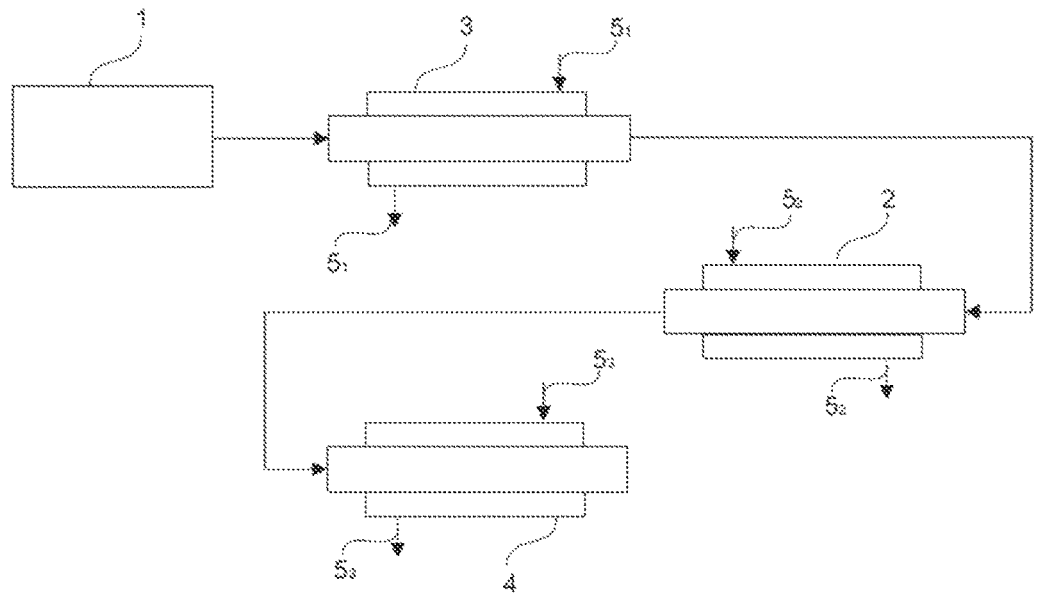
FIG. 1 is an illustration of the system according to one embodiment of the present invention.

The present invention relates to a method for treating a nanofibrillar cellulose hydrogel, wherein the method comprises the steps of: providing a nanofibrillar cellulose hydrogel; and subjecting the nanofibrillar cellulose hydrogel to a heat treatment, wherein the heat treatment is carried out by transferring the nanofibrillar cellulose hydrogel through at least one heat exchanger or through at least one insulated holding tube, during which heat treatment the nanofibrillar cellulose hydrogel is kept at a predetermined temperature within the range of 110-150° C. for a period of time in the range of 15 seconds to 20 minutes, wherein the pre-determined temperature and period of time are chosen such that the number of viable micro-organisms in the nanofibrillar cellulose hydrogel is reduced by a factor of at least $10^3$.

In one embodiment, the method for treating a nanofibrillar cellulose hydrogel comprises the steps of:

providing a nanofibrillar cellulose hydrogel; and subjecting the nanofibrillar cellulose hydrogel to a heat treatment, wherein the heat treatment is carried out by transferring the nanofibrillar cellulose hydrogel through at least one heat exchanger, wherein at least one of the at least one heat exchangers is a scraped surface heat exchanger, or through at least one insulated holding tube, during which heat treatment the nanofibrillar cellulose hydrogel is kept at a predetermined temperature within the range of 110-150° C. for a period of time in the range of 15 seconds to 20 minutes, wherein the pre-determined temperature and period of time are chosen such that the number of viable micro-organisms in the nanofibrillar cellulose hydrogel is reduced by a factor of at least $10^3$.

The present invention further relates to a system for treating a nanofibrillar cellulose hydrogel, wherein the system comprises: a fibrillation unit for providing a nanofibrillar cellulose hydrogel, wherein the fibrillation unit is configured to fibrillate a cellulose-based raw material; and at least one heat exchanger or at least one insulated holding tube for subjecting the nanofibrillar cellulose hydrogel to a heat treatment, wherein the heat treatment is carried out by transferring the nanofibrillar cellulose hydrogel through the at least one heat exchanger or through the at least one insulated holding tube, wherein the heat exchanger or the insulated holding tube is configured to keep the nanofibrillar cellulose hydrogel at a predetermined temperature within the range of 110-150° C. for a period of time in the range of 15 seconds to 20 minutes, wherein the pre-determined temperature and period of time are chosen such that the number of viable micro-organisms in the nanofibrillar cellulose hydrogel is reduced by a factor of at least $10^3$.

In one embodiment, the system for treating a nanofibrillar cellulose hydrogel comprises:

a fibrillation unit for providing a nanofibrillar cellulose hydrogel, wherein the fibrillation unit is configured to fibrillate a cellulose-based raw material; and at least one heat exchanger, wherein at least one of the at least one heat exchangers is a scraped surface heat exchanger, or at least one insulated holding tube for subjecting the nanofibrillar cellulose hydrogel to a heat treatment, wherein the heat treatment is carried out by transferring the nanofibrillar cellulose hydrogel through the at least one heat exchanger or through the at least one insulated holding tube, wherein the heat exchanger or the insulated holding tube is configured to keep the nanofibrillar cellulose hydrogel at a predetermined temperature within the range of 110-150° C. for a period of time in the range of 15 seconds to 20 minutes, wherein the pre-determined temperature and period of time are chosen such that the number of viable micro-organisms in the nanofibrillar cellulose hydrogel is reduced by a factor of at least $10^3$.

In one embodiment, when the system is in use, the fibrillation unit fibrillates the cellulose-based raw material. In one embodiment, when the system is in use, the heating apparatus keeps the nanofibrillar cellulose hydrogel at pre-determined temperature within the range of 110-150° C.

The present invention further relates to the use of a heat treatment for reducing the number of viable micro-organisms in a nanofibrillar cellulose hydrogel, wherein the heat treatment is carried out by transferring the nanofibrillar cellulose hydrogel through at least one heat exchanger or through at least one insulated holding tube, during which heat treatment the nanofibrillar cellulose hydrogel is kept at a predetermined temperature within the range of 110-150° C. for a period of time in the range of 15 seconds to 20 minutes, wherein the pre-determined temperature and period of time are chosen such that the number of viable micro-organisms in the nanofibrillar cellulose hydrogel is reduced by a factor of at least $10^3$.

In one embodiment, the heat treatment is used for reducing the number of viable micro-organisms in a nanofibrillar cellulose hydrogel, wherein the heat treatment is carried out by transferring the nanofibrillar cellulose hydrogel through at least one heat exchanger, wherein at least one of the at least one heat exchangers is a scraped surface heat exchanger, or through at least one insulated holding tube, during which heat treatment the nanofibrillar cellulose hydrogel is kept at a predetermined temperature within the range of 110-150° C. for a period of time in the range of 15 seconds to 20 minutes, wherein the pre-determined temperature and period of time are chosen such that the number of viable micro-organisms in the nanofibrillar cellulose hydrogel is reduced by a factor of at least $10^3$.

The operating pressures are to be selected so that the desired temperature is reached and the nanofibrillar cellulose hydrogel is not boiling in the used temperature. Nanofibrillar cellulose itself is not a volatile component and it does not boil. In one embodiment, the pressure is higher than vapor pressure of water in the nanofibrillar cellulose hydrogel in the desired temperature.

A heat exchanger is an apparatus built for efficient heat transfer from one medium to another. The medium used for heating and/or cooling the desired product, in this case the nanofibrillar cellulose hydrogel, can be separated from the product by a solid wall to prevent mixing or the medium can be in direct contact with the desired product. The medium used for heating and/or cooling the desired product can be e.g. water, oil, or steam.

The heat treatment is carried out by transferring the nanofibrillar cellulose hydrogel through at least one heat exchanger or through at least one insulated holding tube. I.e. the nanofibrillar cellulose hydrogel is transferred into and out from the at least one heat exchanger or the at least one insulated holding tube.

The insulated holding tube is configured to keep the nanofibrillar cellulose hydrogel at a predetermined temperature within the range of 110-150° C. for a period of time in the range of 15 seconds to 20 minutes. The nanofibrillar cellulose hydrogel can be heated to a specific predetermined temperature before being introduced into the insulated holding tube and transferred there through.

The expression "hydrogel" or "nanofibrillar cellulose hydrogel" should be understood in this specification, unless otherwise stated, as referring to an aqueous dispersion of nanofibrillar cellulose having a continuous or discontinuous gel structure. By a "discontinuous" gel structure is to be understood a continuous gel, which is broken into pieces. The hydrogel can be formed by combining nanofibrillar cellulose with e.g. water, buffer solution, cell culture medium or any other aqueous solution optionally supplemented with additives. The storage modulus (G') value of the nanofibrillar cellulose hydrogel is greater than its loss modulus (G") value; i.e. the loss tangent is below 1 at least up to strain value 10%. The storage modulus G', loss modulus G" and loss tangent (G"/G',) of nanofibrillar cellulose hydrogels can be determined with the frequency sweep in dynamic oscillation mode of the rheometer (strain 1% and 10%, frequency 0.1-100, temperature 25° C., pH 7.0). The stress sweep is measured in a shear stress range of 0,001-100 Pa at the frequency 0.1 Hz, and at a temperature of 25° C. and at pH 7. For characterizing the gel forming capacity of a nanofibrillar cellulose the measurement is performed in 0.5 weight-%, 1% strain, frequency of 0.1 Hz. For determining whether a certain material is a gel, i.e. whether its loss tangent is below 1, the measurement is performed in the same way except in the material's consistency. The storage modulus of oxidized nanofibrillar celluloses may vary from 1 to 100 Pa, or from 2 to 50 Pa, or from 5 to 20 Pa, in water at 0.5 weight-% concentration.

The expression "nanofibrillar cellulose" or "NFC" should be understood in this specification, unless otherwise stated, as referring to a collection of isolated cellulose nanofibrils (CNF) or nanofibril bundles derived from cellulose-based raw material.

The fibrils can be isolated from cellulose based raw material. The expression "cellulose-based raw material" should be understood in this specification, unless otherwise stated, as referring to any raw material source that contains cellulose and from which nanofibrillar cellulose can be produced.

In one embodiment, the cellulose-based raw material is based on any plant material that contains cellulose. Plant material may be wood. Wood can be from softwood tree such as spruce, pine, fir, larch, douglas-fir or hemlock, or from hardwood tree such as birch, aspen, poplar, alder, eucalyptus or acacia, or from a mixture of softwoods and hardwoods. Non-wood material can be from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. Depending on the source, different polysaccharide composition may exist in the final nanofibrillar cellulose hydrogel. The nanofibrillar celluloses may contain hemicelluloses and lignin in varying amounts, depending on plant source and pulping conditions.

In one embodiment, the cellulose-based raw material does not contain substantial amounts of lignin. In one embodiment, the nanofibrillar cellulose is essentially free of lignin.

In one embodiment, the cellulose-based raw material is derived from a bacterial fermentation process. In one embodiment, the cellulose based raw material is derived from cellulose-producing micro-organism. The micro-organisms can be of the genus *Acetobacter, Agrobacterium, Rhizobium, Pseudomonas* or *Alcaligenes*, preferably of the genus *Acetobacter*, and more preferably of the species *Acetobacter xylinum* or *Acetobacter pasteurianus*.

Nanofibrils typically have a high aspect ratio. The length might exceed one micrometer while the diameter is typically below 200 nm. The smallest nanofibrils are similar to so called elementary fibrils, which are typically 2-12 nm in diameter. The dimensions of the fibrils or fibril bundles are dependent on raw material and disintegration method. The number average diameter of nanofibrillar cellulose may vary from 1 to 100 nm, such as from 1 to 50 nm, or from 2 to 15 nm. Typically, native or non-derivatized grades have larger diameters and wider fibril size distribution while derivatized grades have smaller diameters and narrower size distributions. Fibril thickness and width distribution may be measured by image analysis of images from a field emission scanning electron microscope (FE-SEM), a transmission electron microscope (TEM), such as a cryogenic transmission electron microscope (cryo-TEM), or an atomic force microscope (AFM).

Nanofibrillar cellulose is characterized by very high water retention values, a high degree of chemical accessibility and the ability to form stable gels, hydrogels, in water or other polar solvents. Nanofibrillar cellulose product is typically a dense network of highly fibrillated cellulose. In an aqueous environment, a dispersion of cellulose nanofibers forms a viscoelastic hydrogel network. The hydrogel is formed at relatively low concentrations of for example 0.05 -0.2% w/w by dispersed and hydrated entangled fibrils.

In one embodiment, the step of providing a nanofibrillar cellulose hydrogel comprises providing a nanofibrillar cellulose hydrogel having a dry-matter content of at least 0.6 weight-%, or at least 0.7 weight-%, or at least 0.8 weight-%, or at least 0.9 weight-%, or at least 1 weight-%. In one embodiment, the step of providing a nanofibrillar cellulose hydrogel comprises providing a nanofibrillar cellulose hydrogel having a dry-matter content of at most 4 weight-%, or at most 3 weight-%, or at most 2 weight-%.

In one embodiment, the nanofibrillar cellulose hydrogel to be subjected to heat treatment has a dry-matter content of at least 0.6 weight-%, or at least 0.7 weight-%, or at least 0.8 weight-%, or at least 0.9 weight-%, or at least 1 weight-%. In one embodiment, the nanofibrillar cellulose hydrogel to be subjected to heat treatment has a dry-matter content of at most 4 weight-%, or at most 3 weight-%, or at most 2 weight-%.

In one embodiment, the nanofibrillar cellulose hydrogel to be subjected to heat treatment has a dry-matter content of 0.6-4 weight-%, or 0.7-3 weight-%, or 0.8-2 weight-%.

In one embodiment, the method comprises a step of pre-heating the nanofibrillar cellulose hydrogel, during which step the nanofibrillar cellulose hydrogel is heated up to a temperature of below 70° C., or below 80° C., or below 90° C., or below 100° C. before subjecting the nanofibrillar cellulose hydrogel to the heat treatment. The step of pre-heating the nanofibrillar cellulose hydrogel can be used for shorten the residence time of the nanofibrillar cellulose hydrogel in the heat treatment. The step of pre-heating the nanofibrillar cellulose hydrogel can be used to make the temperature distribution more even during the treatment of the nanofibrillar cellulose hydrogel. In one embodiment, the step of pre-heating the nanofibrillar cellulose hydrogel is carried out in the same or in a different heat exchanger as the heat treatment. In one embodiment, the step of pre-heating is carried out in at least one heat exchanger. In one embodiment, the step of pre-heating is carried out in two or more heat exchangers.

In one embodiment, the heat treatment is carried out by transferring the nanofibrillar cellulose hydrogel through at least one heat exchanger or through at least one insulated holding tube, in which the nanofibrillar cellulose hydrogel is kept at a predetermined temperature within the range of 121-145° C., or of 121-135° C.

The predetermined temperature and the period of time are chosen such that the number of viable micro-organisms in the nanofibrillar cellulose hydrogel is reduced by a factor of at least $10^3$. In one embodiment, the pre-determined temperature and period of time are chosen such that the number of viable micro-organisms in the nanofibrillar cellulose hydrogel is reduced by a factor of at least $10^6$, or of at least $10^{12}$. In one embodiment, the predetermined temperature and the period of time are chosen such that the number of viable micro-organisms in the nanofibrillar cellulose hydrogel is reduced by a factor of at least $10^6$. In one embodiment, the predetermined temperature and the period of time are chosen such that the number of viable micro-organisms in the nanofibrillar cellulose hydrogel is reduced by a factor of at least $10^{12}$.

The person skilled in the art is capable of determining the specific period of time to be chosen for a specific predetermined temperature to reduce the number of viable micro-organisms in the nanofibrillar cellulose hydrogel by a factor of at least $10^2$, or at least $10^3$, or at least $10^6$, or at least $10^{12}$. As one non-restricting example, reducing the number of viable micro-organisms by heat treatment can be considered to be characterized with two functions and two parameters. The first is based on that the decay of the number of micro-organisms at a certain temperature follows the exponential decay time:

$$N(t) = N(0)e^{-ct}$$

Then, the following parameter is defined:

DT-=decimal reduction time at temperature T This is the time that is required to reduce the number of micro-organisms by one decade $$N_t = \frac{N_0}{10}$$

D-values depend on temperature and they are given at a certain temperature, e.g. $D_{121}$ for T=121° C. The time to reach a certain reduction in the number of viable micro-organisms is denoted with a F-value. If a requirement for a reduction is 12 decades, then the F-value is $$F = 12 D_T$$

The other parameter indicates the dependence of the D-value on temperature. Generally, the higher the temperature is the higher is the death rate. This is defined as the z-value.

$$z = \frac{T_2 - T_1}{-\log_{10}\left(\frac{D_2}{D_1}\right)}$$

By rearranging, $D_2$ is obtained as follows:

$$D_2 = D_1 10^{\frac{T_3 - T_1}{z}}$$

The efficiency of the method can be tested by using certain standard bacteria, e.g. as below indicated:

| | Form | D | D at T | z |
|---|---|---|---|---|
| Aerobic | | | | |
| Staphylococcus aureus | Vegetative cells | 7 min | 60° C. | 9.5° C. |
| Bacillus subtilis | Bacterial spores | 3.7 min | 100° C. | 7.3° C. |
| Pseudomonas aeruginosa | Vegetative cells | 5.07 min | 55° C. | |
| Anaerobic | | | | |
| Clostridinium sporogenes | Spores | 15 min | 110° C. | 12.9° C. |
| Fungi | | | | |
| Candida albicans | | | | |
| Aspergillus niger | Conidium | 0.45 min | 60° C. | 3.7° C. |

D and Z values for the above micro-organisms can be found in the following publications:

*Staphylococcus aureus*: Gaze J. E. (1985) The effect of oil on the heat resistance of Staphylococcus aureus. Food Microbiology 2: 277-283;

*Bacillus subtilis*: Serp D., von Stockar U. and Marison I. W. (2002) Immobilized Bacterial Spores for Use as Bioindicators in the Validation of Thermal Sterilization Processes. Journal of food protection 65: 1134-1141;

*Pseudomonas aeruginosa*: Spinks A. T., Dunstan R. H., Harrison T., Coombes P. and Kuczera G. (2006) Thermal inactivation of water-borne pathogenic and indicator bacteria at sub-boiling temperatures. Water Research 40: 1326-1332;

*Clostridinium sporogenes*: Cameron M. S., Leonard S. J. and Barrett E. L. (1980) Effect of Moderately Acidic pH on Heat Resistance of Clostridium sporogenes Spores in Phosphate Buffer and in Buffered Pea Puree. Applied and Environmental Microbiology 39(5): 943-949; and

*Aspergillus niger*: Shearer A. E. H., Mazzotta A. S., Chuyate R. and Gombas D. E. (2002) Heat resistance of Juice spoilage microorganisms. Journal of food protection 65(8): 1271-1275.

Thus, if a temperature of e.g. 135° C. is used, based on the above table the time required to obtain $F=12D_{135}$ can be estimated. Based on this the below values can be calculated:

| | Form | $D_{135}$ | $F = 12 \times D_{135}$ |
|---|---|---|---|
| Aerobic | | | |
| Staphylococcus aureus | Vegetative cells | <1 sec | <1 sec |
| Bacillus subtilis | Bacterial spores | <1 sec | <1 sec |
| Pseudomonas aeruginosa | Vegetative cells | — | — |
| Anaerobic | | | |
| Clostridinium sporogenes | Spores | 10 sec | 2.1 min |
| Fungi | | | |
| Candida albicans | | — | — |
| Aspergillus niger | Conidium | <1 sec | <1 sec |

In one embodiment, the predetermined temperature and the period of time are chosen such that over-kill conditions of viable micro-organisms are achieved. In one embodiment, the predetermined temperature is about 121° C. and the period of time is about 20 minutes. In one embodiment, the predetermined temperature is about 121° C. and the period of time is about 15 minutes. In one embodiment, the predetermined temperature is about 134° C. and the period of time is about 3 minutes.

In one embodiment, the method comprises, after the heat treatment, the step of cooling the nanofibrillar cellulose hydrogel to a temperature of below 30° C. In one embodiment, the step of cooling the nanofibrillar cellulose hydrogel to a temperature of below 30° C. is carried out in the same or in a different heat exchanger as the heat treatment. In one embodiment, the step of cooling the nanofibrillar cellulose hydrogel is carried out in at least one heat exchanger. In one embodiment, the step of cooling the nanofibrillar cellulose hydrogel is carried out in two or more heat exchangers.

In one embodiment, the nanofibrillar cellulose hydrogel is packed after the step of cooling the nanofibrillar cellulose hydrogel. The cooling has the effect of preventing evaporation of water from the nanofibrillar cellulose hydrogel after it has been packed for storage or for further use.

In one embodiment, at least one of the at least one heat exchangers is a scraped surface heat exchanger. In one embodiment, the heat treatment is carried out in at least one scraped surface heat exchanger. By the use of a scraped surface heat exchanger, rather long running times are achieved due to the continuous scraping of the surface, thus avoiding fouling and achieving a sustainable heat transfer rate during the process. In one embodiment, at least one of the at least one heat exchangers is a plate heat exchanger or a tubular heat exchanger.

In one embodiment, the the nanofibrillar cellulose hydrogel to be subjected to the heat treatment contains at most $10^6$ colony-forming units of a viable micro-organism per gram of nanofibrillar cellulose hydrogel, or at most $10^4$ colony-forming units of a viable micro-organism per gram of nanofibrillar cellulose hydrogel, or at most $10^3$ of a viable micro-organism colony-forming units per gram of nanofibrillar cellulose hydrogel. In one embodiment, the nanofibrillar cellulose hydrogel to be subjected to the heat treatment may contain essentially only aerobic microorganisms. Anaerobes may not be commonly found in nanofibrillar cellulose hydrogels, especially not in wood-derived nanofibrillar cellulose hydrogels.

In one embodiment, providing the nanofibrillar cellulose hydrogel and subjecting the nanofibrillar cellulose hydrogel to heat treatment, and/or to the step of pre-heating and/or to the step of cooling, are carried out while maintaining aseptic conditions. In one embodiment, the fibrillation unit and the heating apparatus are configured to maintain aseptic conditions. Maintaining aseptic conditions may refer to keeping the method for treating nanofibrillar cellulose hydrogel in a closed environment so that the product is transported in pipelines from one production step to the next. Ventilation air and dilution water used should be sterile. E.g. aseptic processing rooms in which air supply, materials, and/or equipment are regulated to control microbial and particle contamination can be used. In one embodiment, the "aseptic conditions" refers to the conditions of ISO 14644-1 cleanroom standard ISO 9, or ISO 8, or ISO 5, or ISO 4, or ISO 3, or ISO 2, or ISO 1. In one embodiment, before the step of subjecting the nanofibrillar cellulose hydrogel to the heat treatment, the conditions of Class ISO 8 or Class ISO 9 are maintained. After the heat treatment maintaining aseptic conditions is even more important than between the steps of providing the nanofibrillar cellulose hydrogel and of subjecting the nanofibrillar cellulose hydrogel to the heat treatment. In one embodiment, after the step of subjecting the nanofibrillar cellulose hydrogel to the heat treatment up to the step of packaging the treated nanofibrillar cellulose hydrogel, the conditions of at least Class ISO 5 are maintained.

In one embodiment, the method for treating a nanofibrillar cellulose hydrogel is carried out in a continuous mode. In one embodiment, the method for treating a nanofibrillar cellulose hydrogel is carried out in a batch mode. In one embodiment, the step of pre-heating, the heat treatment and/or step of cooling are carried out in one and the same heat exchanger in a batch mode. The medium used for heating and/or cooling the nanofibrillar cellulose hydrogel can be supplied in turns for heating and for cooling. In one embodiment, the step of pre-heating, the heat treatment and/or the step of cooling are carried out in continuous mode.

In one embodiment the number of viable micro-organisms in the nanofibrillar cellulose hydrogel is reduced by a factor of at least $10^3$. In one embodiment, the number of viable micro-organisms in the nanofibrillar cellulose hydrogel is reduced by a factor of at least $10^6$. In one embodiment, the number of viable micro-organisms in the nanofibrillar cellulose hydrogel is reduced by a factor of at least $10^{12}$. Pharmaceutical products and medical devices may require sterility of the material or may require that the material is aseptic. As above indicated as absolute sterility cannot be verified, the statistical definition of sterility is used in practice, by using the security assurance level (SAL), defined as "the probability of a single viable micro-organism occurring in or on a product after sterilization". The expression "sterility of the hydrogel" or "sterile" should be understood in this specification, unless otherwise stated, as referring to a nanofibrillar cellulose hydrogel comprising fewer than 1 cfu (colony-forming units), or fewer than $10^{-1}$ cfu, or fewer than $10^{-2}$ cfu, or fewer than $10^{-3}$ cfu, or fewer than $10^-$cfu, or fewer than $10^{-5}$ cfu, or fewer than $10^{-6}$ cfu of a viable microorganism per gram of the nanofibrillar cellulose hydrogel. In other words, if the nanofibrillar cellulose hydrogel comprises fewer than $10^{-6}$ cfu of a viable microorganism per gram of the nanofibrillar cellulose hydrogel, there is a probability of not more than one viable microorganism in one million grams of the nanofibrillar cellulose hydrogel. A "colony-forming unit" is a term that describes the formation of a single macroscopic colony after the introduction of one or more microorganisms to microbiological growth media. One colony forming unit is expressed as 1 CFU.

In one embodiment, the nanofibrillar cellulose is native nanofibrillar cellulose or anionic nanofibrillar cellulose. Anionic nanofibrillar cellulose can be formed by pretreatment replacing at least part of the hydroxyl groups of cellulose with carboxyl groups. In one embodiment, of 10-15% of the hydroxyl groups of cellulose are replaced with carboxyl groups. In one embodiment, the anionic nanofibrillar cellulose is formed by oxidation of cellulose pulp fiber.

Typically, non-ionic or native nanofibrillar cellulose has wider fibril diameter while the chemically modified, anionic nanofibrillar cellulose is much thinner and has a continuous network. The number average fibril diameter of the cellulose nanofibril is suitably from 1-200 nm, preferably the number average fibril diameter of native grades is 1-100 nm, and in chemically modified, anionic grades 1-20 nm. Size distribution is also narrower for the modified grades.

In one embodiment, the method comprises providing a nanofibrillar cellulose hydrogel having a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10rpm.

In one embodiment, the method comprises providing anionic nanofibrillar cellulose hydrogel having a viscosity of 12000-30000 mPa·s as measured at a 0.8% (w/w) concentration of the nanofibrillar cellulose in water with a Brookfield viscometer at a temperature of 20° C., with a vane spindle and a measuring speed of 10 rpm.

The dry matter content (DSC) can be determined by keeping a sample in an oven at a temperature of 105° C. overnight (t=16 h) and by weighting the sample before and after it is kept in the oven. The weighting process is conducted following standard ISO 4119/1995 "Determination of stock concentration", with the difference that the time is 16 h.

The so-called Brookfield viscosity measurement can be determined in the following manner: A vane spindle (number 73) is selected and the Brookfield-viscosity measuring apparatus (Brookfield RVDV-III) is started. A sample of the nanofibrillar cellulose is diluted to a concentration of 0.8% by weight in water and mixed for 10 minutes using a propel mixer 700-800 rpm. No ultrasound mixing is used for modified grades, such as anionic nanofibrillar cellulose. The diluted sample mass is added to a 250 ml beaker and the temperature is adjusted to 20° C. ±1° C., heated if necessary and mixed. The spindle is inserted in the beaker and measuring is started. The program registers 300 points starting with 0.5 rpm speed, then 300 points with 5 rpm and 10 rpm, and 100 points with 50 rpm and 100 rpm speeds. Relative viscosity is measured from each sample mass twice. Mean value and standard deviation are calculated for each sample, from results obtained from parallel measurements during last 5 seconds.

In one embodiment, method comprises providing a nanofibrillar cellulose hydrogel with a turbidity value of at most 200 NTU, or at most 90 NTU, or at most 40 NTU, as measured at a 0.1% (w/w) concentration of the nanofibrillar cellulose in water. In one embodiment, the method comprises providing a nanofibrillar cellulose hydrogel with a turbidity value of 1 to 200 NTU, or 1 to 90 NTU, or 10 to 40 NTU as measured at a 0.1% (w/w) concentration of the nanofibrillar cellulose in water. In one embodiment, method comprises providing a nanofibrillar cellulose hydrogel with a turbidity value of 50 to 500 NTU, or 100 to 150 NTU, as measured at a 0.1% (w/w) concentration of the nanofibrillar cellulose in water. The oxidation level as used according to the present invention has the added utility of making the nanofibrillar cellulose hydrogel obtained through fibrillation homogenous enough and fine enough to reach the above turbidity levels. Nanofibrillar cellulose hydrogel with low turbidity value is beneficial in e.g. medical applications, such as in wound healing or as spread on wounds, and in cell culture applications, such as microscoping or other optical detection applications.

A turbidometric method based on nephelometry (90° angle between light source and detector) can be used for measuring the turbidity of samples. HACH P2100 Turbidometer, with a 50 ml measuring vessel is used for turbidity measurements. The calibration of the apparatus is checked and controlled with standard calibration bottles/samples. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. Mean value and standard deviation are calculated for each sample.

In one embodiment, the viscosity of the nanofibrillar cellulose hydrogel, after the heat treatment, differs at most 50%, or at most 30%, or at most 10%, or at most 5%, from the viscosity of the nanofibrillar cellulose hydrogel before the heat treatment, when the dry matter content of the nanofibrillar cellulose hydrogel subjected to the heat treatment is at least 0.6 weight-% and when the viscosity after the heat treatment is measured in the same dry matter content of at least 0.6 weight-%. I.e. the viscosity is measured in the same dry matter content before and after the heat treatment. The inventor of the present invention surprisingly found out that the heat treatment carried out in a heat exchanger, and especially in a scraped surface heat exchanger, or in an insulated holding tube may not affect the viscosity of the hydrogel in an adverse manner in view of its further use in e.g. pharmaceutical or cosmetic products, or in cell culture.

In one embodiment, providing the nanofibrillar cellulose hydrogel comprises fibrillation of cellulose-based raw material. In one embodiment the nanofibrillar cellulose hydrogel is provided by fibrillation of cellulose pulp or refined pulp. Cellulose pulp can be used as cellulose-based raw material. Cellulose pulp can be formed by isolating cellulose fibers from raw material that contains cellulose by chemical, mechanical, thermo-mechanical, or chemithermo mechanical pulping processes, e.g. kraft pulping, sulfate pulping, soda pulping, organosolv pulping, and by conventional bleaching processes. In one embodiment fibrillation of cellulose-based raw material is carried out with a refiner, grinder, homogenizer, colloider, friction grinder, ultrasound sonicator, fluidizer such as microfluidizer, macrofluidizer or fluidizer-type homogenizer. In one embodiment of the present invention the step of pre-refining cellulose-based raw material is preceding the step of fibrillating the cellulose-based raw material.

The dimensions of the fibrils or fibril bundles of the nanofibrillar cellulose are dependent on the raw material and the fibrillation method. The term fibrillation may be used interchangeably with expression disintegration, and generally refers to disintegrating cellulose-based raw material mechanically by work applied to the fibers, where cellulose fibrils are liberated from the fibers or fiber fragments. The work may be based on various effects, like grinding, crushing or shearing, or a combination of these, or another corresponding action that delaminates the cell walls of the fibers and liberates fibrils. The energy taken by the refining work is normally expressed in terms of energy per processed raw material quantity, in units of e.g. kWh/kg, MWh/ton, or units proportional to these. The disintegration is performed at conditions wherein water is sufficiently present to prevent the formation of bonds between the fibers.

In one embodiment, the system comprises a heat exchanger configured to heat the nanofibrillar cellulose hydrogel up to a temperature of below 70° C., or below 80° C., or below 90° C., or below 100° C., before subjecting the nanofibrillar cellulose hydrogel to the heat treatment.

In one embodiment, the heat exchanger or the insulating holding tube is configured to keep the nanofibrillar cellulose hydrogel at a predetermined temperature within the range of 121-145° C., or of 121-135° C.

In one embodiment, the system comprises a heat exchanger configured to cool the nanofibrillar cellulose hydrogel to a temperature of below 30° C. after the heat treatment.

In one embodiment, the system comprises a packaging unit for packaging the treated nanofibrillar cellulose hydrogel. In one embodiment, the packaging unit is configured to package the treated nanofibrillar cellulose hydrogel. In one embodiment, the packaging unit packages the treated nanofibrillar cellulose hydrogel when in use.

The present invention further relates to a nanofibrillar cellulose hydrogel obtainable by the method according to the present invention.

In one embodiment, the nanofibrillar cellulose hydrogel obtainable by the method according to the present invention, has a viscosity, after the heat treatment, which differs at most 30%, from the viscosity of the nanofibrillar cellulose hydrogel before the heat treatment, when the dry matter content of the nanofibrillar cellulose hydrogel subjected to the heat treatment is at least 0.6 weight-% and when the viscosity after the heat treatment is measured in the same dry matter content of at least 0.6 weight-%.

The present invention further relates to a nanofibrillar cellulose hydrogel, wherein the nanofibrillar cellulose hydrogel contains no colony-forming units of a viable micro-organism per gram of the nanofibrillar cellulose hydrogel, as measured by culturing on a growth medium, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm. This kind of nanofibrillar cellulose hydrogel can be produced by the method described in this specification.

The presence of viable micro-organisms in the nanofibrillar cellulose hydrogel can be determined by culturing on a growth medium. Several protocols for determining the number of colony forming units are available.

In an embodiment, the number of colony-forming units per gram of nanofibrillar cellulose hydrogel is determined by preparing a dilution series of the hydrogel and by plating the dilution series on separate Petrifilm plates (3M) for aerobic bacteria (aerobic plate count) and for yeasts and moulds. The plates for aerobic bacteria are allowed to grow at 37° C. for 2 days and the plates for yeasts and moulds at 30° C. for 3-5 days, after which the colonies are counted. The number of colony-forming units of aerobic heterotrophs are determined by culturing the sample on plate count agar at a temperature of 37° C. for three (3) days. Alternatively, the presence of yeast and/or fungus can be determined by culturing on potato dextrose agar at a temperature of 25° C. for five (5)

days. Before the measurement, the samples are diluted by ten-fold. The presence of anaerobic micro-organisms can be determined by culturing on brewer anaerobic agar for anaerobic bacterial count at a temperature of 30° C. for three (3) days in anaerobic conditions. Before the measurement, the samples are diluted ten-fold.

In an embodiment, the number of colony-forming units is determined by following the standard ISO 8784-1 (Pulp, Paper and board-Microbiological examination. Part 1: Total count of bacteria, yeast and mould based on disintegration). The results are given as the number of colony-forming units per gram of the sample.

In an embodiment, the number of colony-forming units of viable micro-organism per gram of nanofibrillar cellulose hydrogel may be measured by incubating at 37° C. for 14 days following the USP XXIV Chapter 71 sterility test.

The present invention further relates to a nanofibrillar cellulose hydrogel for use in therapy, wherein the nanofibrillar cellulose hydrogel contains at most $10^{-2}$ colony-forming units of a viable micro-organism per gram of the nanofibrillar cellulose hydrogel, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm. In one embodiment, the nanofibrillar cellulose hydrogel for use in therapy contains at most $10^{-3}$, or at most $10^{-6}$, colony-forming units of a viable micro-organism per gram of the nanofibrillar cellulose hydrogel.

The present invention further relates to a nanofibrillar cellulose hydrogel obtainable by the method according to the present invention for use in therapy.

In one embodiment, the nanofibrillar cellulose hydrogel obtainable by the method according to the present invention for use in therapy, has a viscosity, after the heat treatment, which differs at most 30%, from the viscosity of the nanofibrillar cellulose hydrogel before the heat treatment, when the dry matter content of the nanofibrillar cellulose hydrogel subjected to the heat treatment is at least 0.6 weight-% and when the viscosity after the heat treatment is measured in the same dry matter content of at least 0.6 weight-%.

The present invention further relates to the use of a nanofibrillar cellulose hydrogel in a cosmetic product, wherein the nanofibrillar cellulose hydrogel contains no colony-forming units of a viable micro-organism per gram of the nanofibrillar cellulose hydrogel, as measured by culturing on a growth medium, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm.

The present invention further relates to the use of a nanofibrillar cellulose hydrogel obtainable by the method according to the present invention in a cosmetic product.

In one embodiment, the nanofibrillar cellulose hydrogel obtainable by the method according to the present invention is used in a cosmetic product, wherein the viscosity of the nanofibrillar cellulose hydrogel, after the heat treatment, differs at most 30%, from the viscosity of the nanofibrillar cellulose hydrogel before the heat treatment, when the dry matter content of the nanofibrillar cellulose hydrogel subjected to the heat treatment is at least 0.6 weight-% and when the viscosity after the heat treatment is measured in the same dry matter content of at least 0.6 weight-%.

The present invention further relates to the use of a nanofibrillar cellulose hydrogel in cell culture, wherein the nanofibrillar cellulose hydrogel contains at most $10^2$ colony-forming units of a viable micro-organism per gram of the nanofibrillar cellulose hydrogel, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm.

The present invention further relates to the use of a nanofibrillar cellulose hydrogel obtainable by the method according to the present invention in cell culture.

In one embodiment, the nanofibrillar cellulose hydrogel obtainable by the method according to the present invention is used in cell culture, wherein the viscosity of the nanofibrillar cellulose hydrogel, after the heat treatment, differs at most 30%, from the viscosity of the nanofibrillar cellulose hydrogel before the heat treatment, when the dry matter content of the nanofibrillar cellulose hydrogel subjected to the heat treatment is at least 0.6 weight-% and when the viscosity after the heat treatment is measured in the same dry matter content of at least 0.6 weight-%.

In one embodiment, the nanofibrillar cellulose hydrogel, which is used in cell culture, contains at most $10^{-3}$, or at most $10^{-6}$, colony-forming units of viable micro-organism per gram of the nanofibrillar cellulose hydrogel.

The embodiments of the invention described hereinbefore may be used in any combination with each other. Several of the embodiments may be combined together to form a further embodiment of the invention. A method, a hydrogel, a system, or a use, to which the invention is related, may comprise at least one of the embodiments of the invention described hereinbefore.

An advantage of the method according to the present invention is that the nanofibrillar cellulose hydrogel can be treated in order to reduce the number of viable micro-organisms therein without compromising, in an adverse extent, other properties such as viscosity thereof.

An advantage of the method according to the present invention is that in addition to reducing the number of viable micro-organisms in the nanofibrillar cellulose hydrogel, also any possibly present proteins are denaturated and thus inactivated.

An advantage of the method according to the present invention is that the heat treatment can easily be combined with the step of providing the nanofibrillar cellulose hydrogel as well as e.g. the packaging step thereof following the heat treatment.

An advantage of the method according to the present invention is that a nanofibrillar cellulose hydrogel can be provided for use in pharmaceutical or cosmetic applications. An advantage of the method according to the present invention is that biocides are not needed to reduce the number of viable micro-organisms in the nanofibrillar cellulose hydrogel. In some cases, depending on the end-use of the treated nanofibrillar cellulose hydrogel, a minor amount of biocide can be used in order to reach a required purity level.

EXAMPLES

Reference will now be made in detail to the embodiments of the present invention, an example of which is illustrated in the accompanying drawing.

The description below discloses some embodiments of the invention in such a detail that a person skilled in the art is able to utilize the invention based on the disclosure. Not all steps of the embodiments are discussed in detail, as many of the steps will be obvious for the person skilled in the art based on this specification.

For reasons of simplicity, item numbers will be maintained in the following exemplary embodiments in the case of repeating components.

FIG. 1 illustrates a system according to one embodiment of the present invention for treating a nanofibrillar cellulose hydrogel. The system comprises a fibrillation unit 1 for providing a nanofibrillar cellulose hydrogel. The fibrillation unit is configured to fibrillate a cellulose-based raw material. The cellulose-based raw material can be e.g. cellulose pulp, which is disintegrated in e.g. a fluidizer or homogenizer.

The produced nanofibrillar cellulose hydrogel is then provided into heat exchanger 3, where it is pre-heated up to a temperature of below 70° C., or below 80° C., or below 90° C., or below 100° C., before subjecting the nanofibrillar cellulose hydrogel to the heat treatment.

The heat treatment is then carried out in a heat exchanger 2, which in this embodiment is a different heat exchanger than where the step of pre-heating is carried out. The heat exchanger keeps the nanofibrillar cellulose hydrogel at a predetermined temperature within the range of 110-150° C. for a period of time in the range of 15 seconds to 20 minutes. The predetermined temperature and period of time are chosen such that the number of viable micro-organisms in the nanofibrillar cellulose hydrogel is reduced by a factor of at least $10^3$.

The system further comprises a heat exchanger 4, which in this embodiment is different from the ones used for the step of pre-heating and for the heat treatment, which is used to cool the nanofibrillar cellulose hydrogel to a temperature of below 30° C. after the heat treatment.

The nanofibrillar cellulose hydrogel is transferred from one unit or heat exchanger to another. I.e. the nanofibrillar cellulose hydrogel is introduced into and out from each of the heat exchangers.

The system could further comprise e.g. a packaging unit for packaging the treated nanofibrillar cellulose hydrogel.

The system presented in FIG. 1 is configured to maintain aseptic conditions.

In this embodiment, different heat exchangers are used for the step of pre-heating, the heat treatment, and the step of cooling. However, these steps could equally well be carried out by using e.g. only one heat exchanger. If only one heat exchanger is used to carry out the above steps, the medium used in the heat exchanger for heating and cooling the hydrogel may vary or at least its temperature is varied depending on which step is to be carried out. The medium can be e.g. steam, oil, or water. In FIG. 1, the small arrows $5_1$, $5_2$, $5_3$ pointing into and out from each of the heat exchangers 2, 3, 4 are to indicate the direction of putting medium in to and out from each of the heat exchangers.

The system could additionally comprise more than one heat exchanger for subjecting the nanofibrillar cellulose hydrogel to the step of pre-heating the nanofibrillar cellulose hydrogel. The system could comprise more than one heat exchanger for subjecting the nanofibrillar cellulose hydrogel to the heat treatment. The system could comprise more than one heat exchanger for subjecting the nanofibrillar cellulose hydrogel to the step of cooling the nanofibrillar cellulose hydrogel.

Also, instead of the heat exchanger, the heat treatment could be carried out by using an insulated holding tube.

Example 1

Heat Treatment of Anionic Nanofibrillar Cellulose Hydrogel

The effect of heat treatment carried out in a heat exchanger on the properties of anionic nanofibrillar cellulose hydrogel was tested.

Firstly, bleached birch pulp (bale pulp) was TEMPO-oxidized to the oxidation level of 1000 μmol COOH/g dry pulp. So-called TEMPO-oxidation is a well-known process in the art. TEMPO-oxidation is catalytic oxidation of cellulose carried out by using a heterocyclic nitroxyl radical, i.e. 2,2,6,6-tetramethylpiperidinyl-1-oxy free radical.

After the oxidation treatment, the pulp was fibrillated to produce nanofibrillar cellulose hydrogels. The fibrillation was continued until a viscose hydrogel was formed. The manufacturing consistency was 2.5 weight-%. The nanofibrillar cellulose hydrogel was diluted with strong mixing and using deionized water to either 1.5 weight-% (sample A-1) or 1.0 weight-% (sample A-2).

A sample B was also made and it was a diluted form of sample A. The dilution to 0.5% consistency was done with an industrial scale mixing device using tap water.

The viscosity of the formed samples were determined by measuring the Brookfield viscosity as above described. The results are shown in table 1.

Then the samples were introduced into a scraped surface heat exchanger (Armfield FT25), where they were either subjected to a heat treatment at a temperature of 121° C. for 15 minutes or to a heat treatment at a temperature of 134° C. for 3 minutes. Due to the required heating and cooling of the samples, both of them spend about 25 minutes at a temperature of above 100° C.

The viscosity of the treated samples was determined by measuring the Brookfield viscosity at 10 rpm in a manner as above described in the same dry matter content as above described; i.e. 1.5 weight-% for sample A-1, 1.0 weight-% for sample A-2 and 0.5 weight-% for sample B. The results are shown in table 1.

TABLE 1

| | | Brookfield viscosities | | | | | |
|---|---|---|---|---|---|---|---|
| | | 1st parallel of hydrogel | | | 2nd parallel of hydrogel | | |
| | | | Viscosity (mPas) | | | | Viscosity (mPas) |
| | Sample | DSC (w-%) | Initial | After (difference in viscosity) | Sample | DSC (w-%) | Initial | After (difference in viscosity) |
| 121° C. 15 min | A-1 | 1.5 | 48200 | 46500 (−5%) | A-1 | 1.5 | 52200 | 41650 (−20%) |
| | A-2 | 1.0 | 21000 | 19200 (−9%) | A-2 | 1.0 | 23100 | 22100 (−4%) |
| | B | 0.5 | 3050 | 1850 (−39%) | B | 0.5 | 2830 | 1070 (−62%) |

TABLE 1-continued

Brookfield viscosities

| | 1st parallel of hydrogel | | | 2nd parallel of hydrogel | | | |
|---|---|---|---|---|---|---|---|
| | | | Viscosity (mPas) | | | | Viscosity (mPas) |
| Sample | | DSC (w-%) | Initial | After (difference in viscosity) | Sample | DSC (w-%) | Initial | After (difference in viscosity) |
| 134° C. 3 min | A-1 | 1.5 | 47200 | 46500 (−1%) | A-1 | 1.5 | 48000 | 33120 (−31%) |
| | A-2 | 1.0 | 27700 | 18550 (−33%) | A-2 | 1.0 | 22300 | 20000 (−10%) |
| | B | 0.5 | 2750 | 3235 (+18%) | B | 0.5 | 4300 | 1690 (−61%) |

From the results indicated in table 1, it can be seen that the heat treatment in the heat exchanger does not affect the viscosity to an adverse extent when the dry matter content of the nanofibrillar cellulose hydrogel is 1.0 weight-% or 1.5 weight-%. In these samples, the nanofibrillar cellulose hydrogels have maintained their character during the heat treatment. It was also found that heat treatment reduced the number of viable micro-organisms in the nanofibrillar cellulose hydrogel.

Example 2

Heat Treatment of Native Nanofibrillar Cellulose Hydrogel

The effect of heat treatment carried out in a heat exchanger on the properties of native nanofibrillar cellulose hydrogel was tested.

Native bleached birch pulp (bale pulp) was fibrillated to form nanofibrillated cellulose hydrogel of three different degrees of fineness. The manufactured dry matter content was 1.15 weight-%.

The three different samples were heat treated in a similar manner as described in Example 1 by subjecting the samples to a temperature of 121° C. for 20 minutes.

The heat treated samples were tested and the results can be seen in table 2.

TABLE 2

Properties of the nanofibrillar cellulose hydrogel before and after the heat treatment

| | Sample 1 | | Sample 2 | | Sample 3 | |
|---|---|---|---|---|---|---|
| | before | after | before | after | before | after |
| Brookfield, 10 rpm, 1.15% dsc (Pa · s) | 20.6 | 21.0 | 21.4 | — | 21.5 | 21.2 |

From the results it can be seen that in the manufactured consistency there is practically no changes in the viscosity of the nanofibrillar celluose hydrogel.

Example 3

Heat Treatment of Nanofibrillar Cellulose Hydrogel with Different Dry-matter Contents In this example the effect of heat treatment in the heat exchanger was tested by using nanofibrillar cellulose hydrogels having different dry-matter contents. Sample B from Example 2 was used as a basis. The heat treatment was carried out using two different temperatures, i.e. 121° C. and 135° C.

Figure 2:
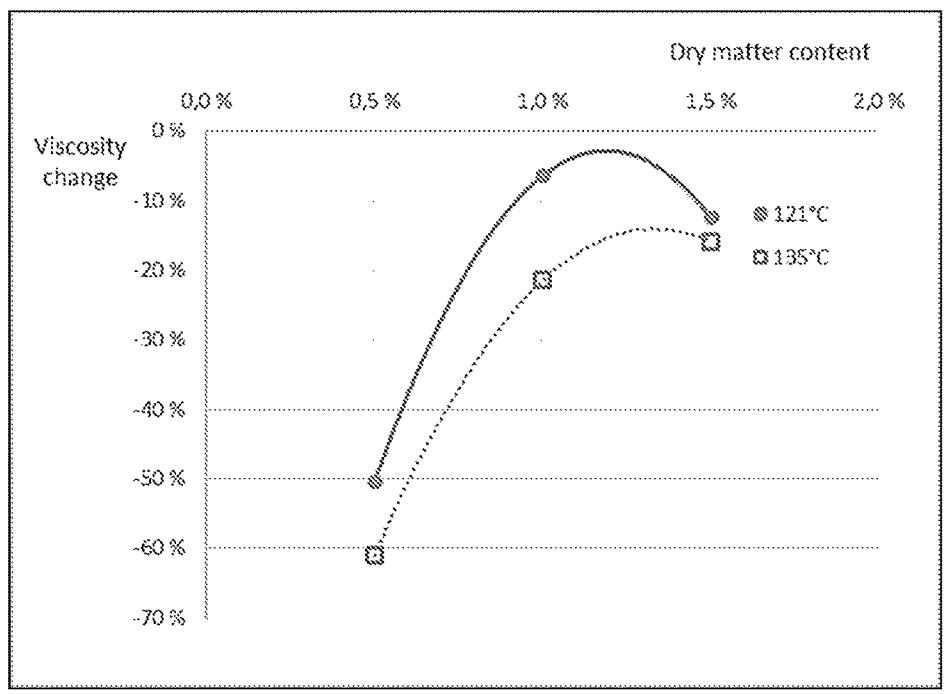
FIG. 2 illustrates the relationship between the dry matter content of the nanofibrillar cellulose hydrogel and the change in viscosity as a result of the heat treatment carried out in a heat exchanger.

From the results presented in FIG. 2, it can be seen that with a lower dry matter content, the change in the viscosity as a result of the heat treatment is larger than when using a higher dry matter content.

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A method for treating a nanofibrillar cellulose hydrogel, wherein the method comprises the steps of:
   providing a nanofibrillar cellulose hydrogel; and
   subjecting the nanofibrillar cellulose hydrogel to a heat treatment, wherein the heat treatment is carried out by transferring the nanofibrillar cellulose hydrogel through at least one heat exchanger, wherein at least one of the at least one heat exchangers is a scraped surface heat exchanger, or through at least one insulated holding tube, during which heat treatment the nanofibrillar cellulose hydrogel is kept at a predetermined temperature within the range of 110-150° C. for a period of time in the range of 15 seconds to 20 minutes, wherein the pre-determined temperature and period of time are chosen such that the number of viable micro-organisms in the nanofibrillar cellulose hydrogel is reduced by a factor of at least $10^3$.

2. The method of claim 1, wherein the step of providing a nanofibrillar cellulose hydrogel comprises providing a nanofibrillar cellulose hydrogel having a dry-matter content of at least 0.6 weight-%.

3. The method of claim 1, wherein the step of providing a nanofibrillar cellulose hydrogel comprises providing a nanofibrillar cellulose hydrogel having a dry-matter content of at most 4 weight-%.

4. The method of claim 1, wherein the method comprises a step of pre-heating the nanofibrillar cellulose hydrogel, during which step the nanofibrillar cellulose hydrogel is heated up to a temperature of below 100° C., before subjecting the nanofibrillar cellulose hydrogel to the heat treatment.

5. The method of claim 1, wherein the heat treatment is carried out by transferring the nanofibrillar cellulose through at least one heat exchanger or through at least one insulated holding tube, in which the nanofibrillar cellulose hydrogel is kept at a predetermined temperature within the range of 121-145° C.

6. The method of claim 1, wherein the method comprises, after the heat treatment, the step of cooling the nanofibrillar cellulose hydrogel to a temperature of below 30° C.

7. The method of claim 1, wherein providing the nanofibrillar cellulose hydrogel and subjecting the nanofibrillar cellulose hydrogel to heat treatment are carried out while maintaining aseptic conditions.

8. The method of claim 1, wherein the pre-determined temperature and period of time are chosen such that the number of viable micro-organisms in the nanofibrillar cellulose hydrogel is reduced by a factor of at least $10^6$.

9. The method of claim 1, wherein the viscosity of the nanofibrillar cellulose hydrogel, after the heat treatment, differs at most 50% from the viscosity of the nanofibrillar cellulose hydrogel before the heat treatment, when the dry matter content of the nanofibrillar cellulose hydrogel subjected to the heat treatment is at least 0.6 weight-% and when the viscosity after the heat treatment is measured in the same dry matter content of at least 0.6 weight-%.

10. The method of claim 1, wherein providing the nanofibrillar cellulose hydrogel comprises fibrillation of a cellulose-based raw material.

11. A system for treating a nanofibrillar cellulose hydrogel, wherein the system comprises:
a fibrillation unit for providing a nanofibrillar cellulose hydrogel, wherein the fibrillation unit is configured to fibrillate a cellulose-based raw material; and
at least one heat exchanger, wherein at least one of the at least one heat exchangers is a scraped surface heat exchanger, or at least one insulated holding tube for subjecting the nanofibrillar cellulose hydrogel to a heat treatment, wherein the heat treatment is carried out by transferring the nanofibrillar cellulose hydrogel through the at least one heat exchanger or through the at least one insulated holding tube, wherein the heat exchanger or the insulated holding tube is configured to keep the nanofibrillar cellulose hydrogel at a predetermined temperature within the range of 110-150° C. for a period of time in the range of 15 seconds to 20 minutes, wherein the pre-determined temperature and period of time are chosen such that the number of viable micro-organisms in the nanofibrillar cellulose hydrogel is reduced by a factor of at least $10^3$.

12. The system of claim 11, wherein the system comprises a heat exchanger configured to heat the nanofibrillar cellulose hydrogel up to a temperature of below 70° C. before subjecting the nanofibrillar cellulose hydrogel to the heat treatment.

13. The system of claim 11, wherein the heat exchanger or the insulated holding tube is configured to keep the nanofibrillar cellulose hydrogel at a predetermined temperature within the range of 121-145° C.

14. The system of claim 11, wherein, the system comprises a heat exchanger configured to cool the nanofibrillar cellulose hydrogel to a temperature of below 30° C. after the heat treatment.

15. Use of a heat treatment for reducing the number of viable micro-organisms in a nanofibrillar cellulose hydrogel, wherein the heat treatment is carried out by transferring the nanofibrillar cellulose hydrogel through at least one heat exchanger, wherein at least one of the at least one heat exchangers is a scraped surface heat exchanger, or through at least one insulated holding tube, during which heat treatment the nanofibrillar cellulose hydrogel is kept at a predetermined temperature within the range of 110-150° C. for a period of time in the range of 15 seconds to 20 minutes, wherein the pre-determined temperature and period of time are chosen such that the number of viable micro-organisms in the nanofibrillar cellulose hydrogel is reduced by a factor of at least $10^3$.

* * * * *